United States Patent
Eckerdal

(10) Patent No.: US 8,527,066 B2
(45) Date of Patent: Sep. 3, 2013

(54) MEDICAL IMPLANTABLE LEAD AND A METHOD FOR ENSURING PROPER AND SAFE ATTACHMENT OF SUCH A LEAD TO AN ORGAN

(75) Inventor: Johan Eckerdal, Knivsta (SE)

(73) Assignee: St. Jude Medical AB, Jarfalla (SE)

( * ) Notice: Subject to any disclaimer, the term of this patent is extended or adjusted under 35 U.S.C. 154(b) by 109 days.

(21) Appl. No.: 13/140,746

(22) PCT Filed: Dec. 19, 2008

(86) PCT No.: PCT/SE2008/000729
§ 371 (c)(1),
(2), (4) Date: Jun. 17, 2011

(87) PCT Pub. No.: WO2010/071494
PCT Pub. Date: Jun. 24, 2010

(65) Prior Publication Data
US 2011/0264179 A1    Oct. 27, 2011

(51) Int. Cl.
*A61N 1/05* (2006.01)
(52) U.S. Cl.
USPC ............ 607/116; 607/126; 607/127; 128/899
(58) Field of Classification Search
USPC .......................................... 607/119–138, 116
See application file for complete search history.

(56) References Cited

U.S. PATENT DOCUMENTS

| | | |
|---|---|---|
| 3,974,834 A | 8/1976 | Kane |
| 4,972,848 A | 11/1990 | Domenico et al. |
| 5,649,975 A | 7/1997 | Lindegren et al. |
| 5,948,015 A | 9/1999 | Hess et al. |
| 2003/0065374 A1 | 4/2003 | Honeck |
| 2007/0219551 A1* | 9/2007 | Honour et al. .................. 606/41 |

FOREIGN PATENT DOCUMENTS

WO    WO 2004/028348    4/2004

* cited by examiner

*Primary Examiner* — Kennedy Schaetzle
*Assistant Examiner* — Erica Lee

(57) ABSTRACT

A medical implantable lead of the kind being adapted to be implanted into a human or animal body for monitoring and/or controlling of an organ inside the body has a penetrating fixation element in a distal end, which is adapted to penetrate into the tissue of the organ to fixate the lead such that a distal end of the lead will be in contact with the organ. The lead also has an electrode member to receive and/or transmit electrical signals from and/or to the organ. The lead has in a distal portion a movable member, which is displaceable in an axial direction of the lead and is actuated by a resilient member to be, in an initial state, maximally protruded in a distal direction in relation to the lead and which comprises a radiopaque material for forming of a first indication marker. The lead also has a second indication marker of a radiopaque material in relation to which the movable member is displaceable, and the first and the second indication markers are arranged such that, when observing the lead in an implanted state by means of fluoroscopy, it will be recognizable from the relative positions of the first and second indication markers, whether the distal end of the lead is in close contact with the surface of the tissue or not. A comparable method ensures proper and safe attachment of a medical implantable lead to an organ.

9 Claims, 7 Drawing Sheets

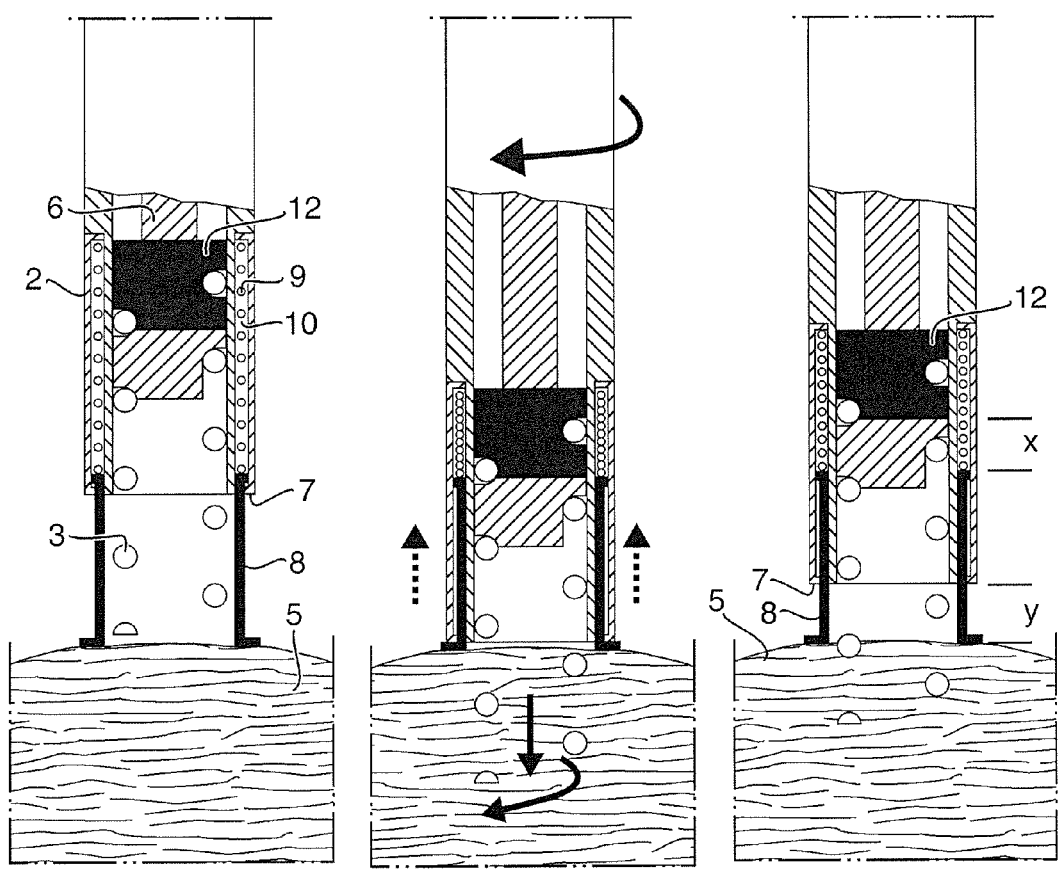

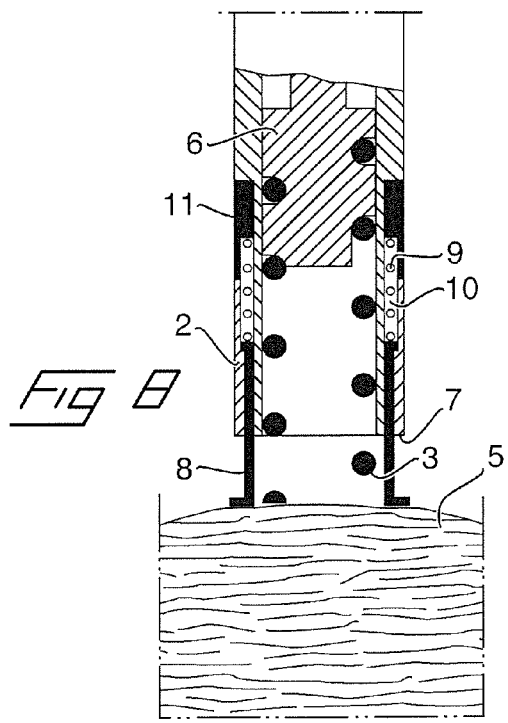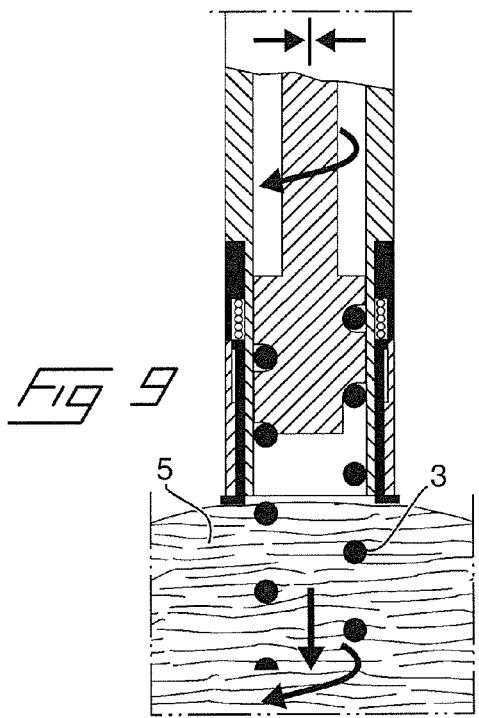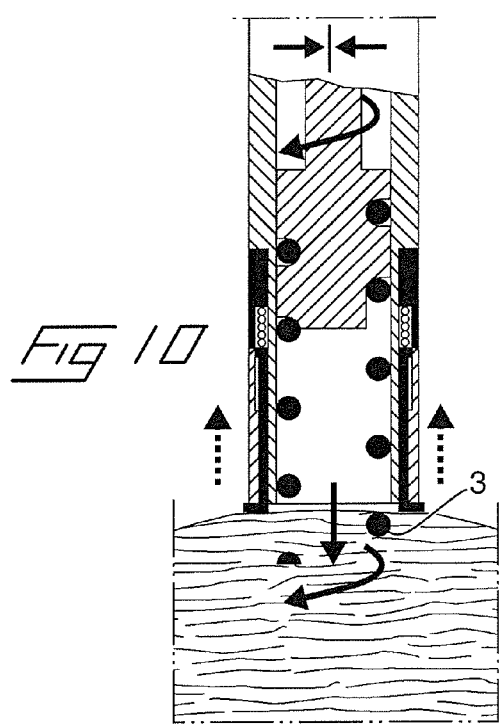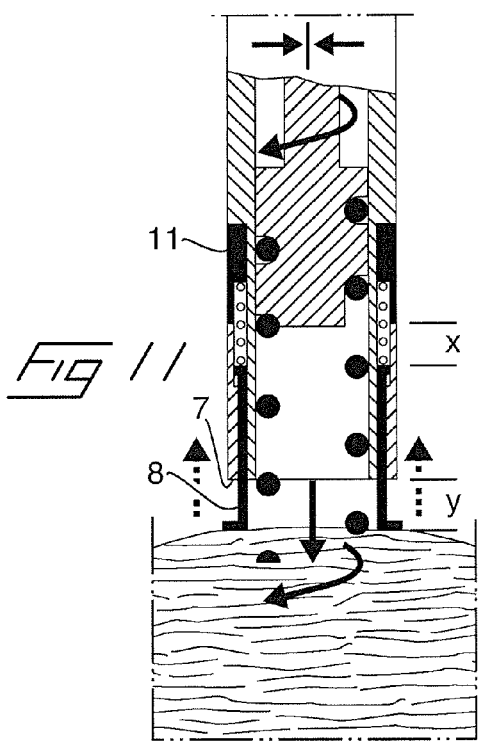

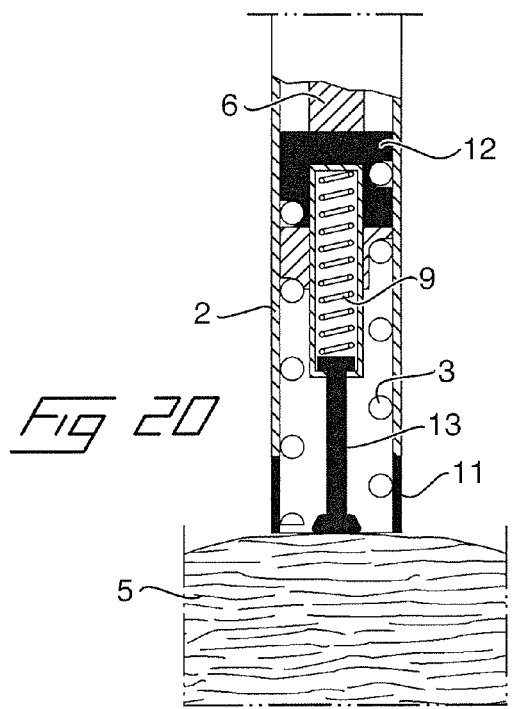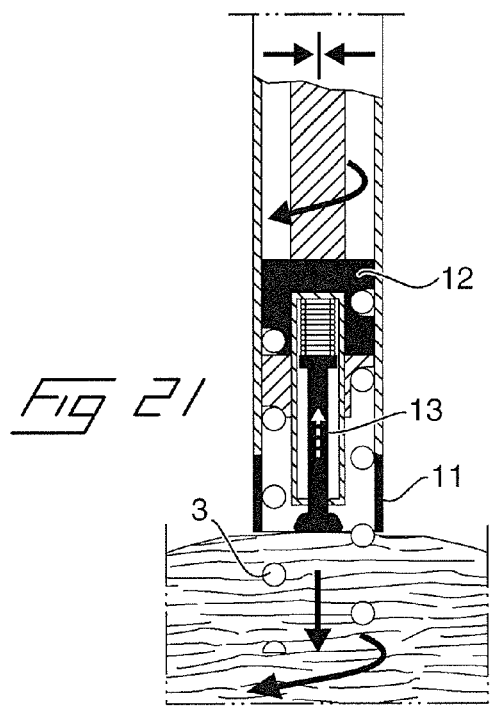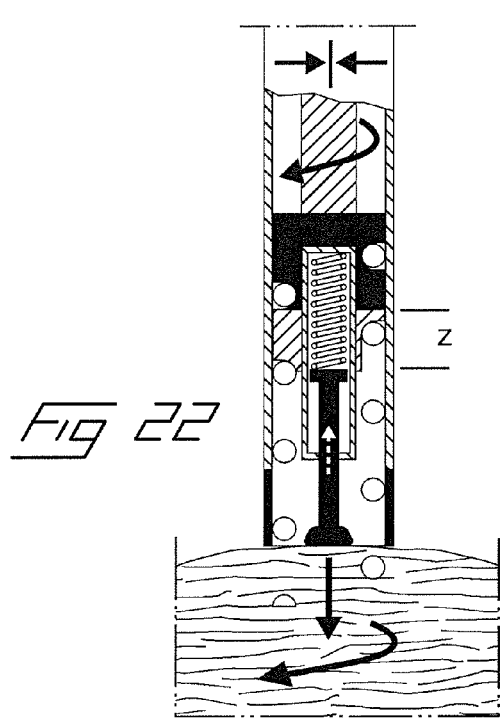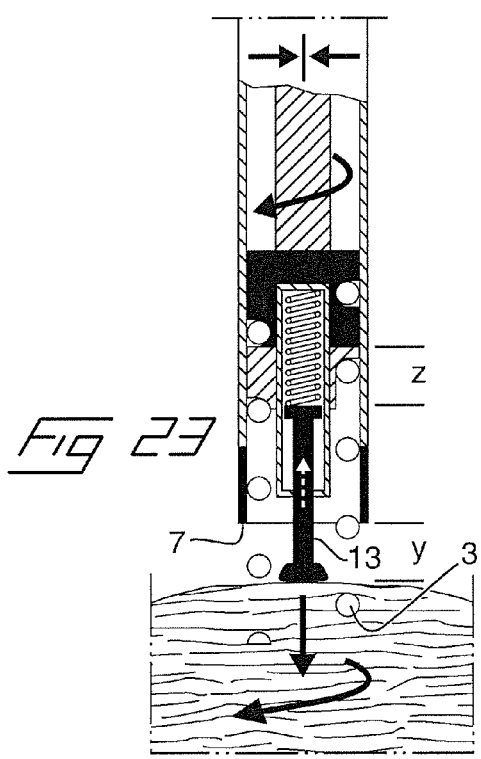

MEDICAL IMPLANTABLE LEAD AND A METHOD FOR ENSURING PROPER AND SAFE ATTACHMENT OF SUCH A LEAD TO AN ORGAN

BACKGROUND OF THE INVENTION

1. Field of the Invention

The present invention relates to a medical implantable lead of the kind being adapted to be implanted into a human or animal body for monitoring and/or controlling of an organ inside the body, having a penetrating fixation element in a distal end, which is adapted to penetrate into the tissue of the organ to fixate the lead such that a distal end of the lead will be in contact with the organ, an electrode member to receive and/or transmit electrical signals from and/or to the organ, and an indication arrangement of a radiopaque material for visibility by means of fluoroscopy in an implanted state.

The invention also relates to a method for ensuring proper and safe attachment of a medical implantable lead to an organ inside a human or animal body.

2. Description of the Prior Art

Within the area of medical implantable leads, it is common practice to use a penetrating fixation element to fixate the lead to an organ to be monitored and/or controlled, i.e. the lead is fixated to the organ by means of a fixation element which is penetrated into the organ for engaging the tissue and maintain the lead in electrical contact with the organ. Normally, the fixation element has the form of a helix, which is screwed into the tissue, but also other types of penetrating fixation element can be conceivable, such as straight and sharp fixation element having barbs and the like. Moreover, the penetrating fixation element may also function as an electrode, which is to be embedded into tissue and receive and/or transmit electrical signals from and to the tissue, respectively.

When fixating a medical implantable lead to an organ by means of a penetrating fixation element, it is important that the penetrating fixation element is completely embedded into tissue. This is important for the mechanical stability, in order to permit the lead to be maintained fixated to the organ during a long period of time. This is also important for the electrical performance, in the case of the penetrating fixation element itself being an electrode, or if an electrode surface on the distal end of the lead is to be held in close contact with the tissue. Moreover, if the penetrating fixation element functions as an electrode, the impedance of the electrode will be reduced in case the electrode is not completely embedded into tissue but instead the electrode is at least partly in contact with e.g. free blood or other body fluids. Reduced impedance will increase the energy consumption when transmitting signals between the organ and a monitoring and/or controlling device, which normally is battery operated.

If the penetrating fixation element is a helix, which is screwed into the tissue, there is a risk that the physician performing the attachment may apply too much torque to the helix in order to be sure that the helix is completely embedded into the tissue. This may cause damage to the tissue in form of tearing or perforation of the tissue if the organ has a comparatively thin wall, such as is the case with e.g. a heart.

In prior art, medical implantable leads are known having a penetrating fixation element in form of a helix, which is rotatable in relation to the lead and at the same time extendable out from a cavity in a so called header sleeve in the distal end of the lead. In order for the physician performing the attachment to see when the helix is completely extended from the header sleeve, an indication arrangement of a radiopaque material is provided which can be seen by means of fluoroscopy during implantation. The indication arrangement has a fixed indication marker positioned on the header, e.g. shaped as a ring, and a movable indication marker positioned on or forming the helix or a shaft on which the helix is mounted. During implantation, the physician can see the fixed and the movable indication markers by fluoroscopy, and when a predetermined number of helix coils is visible beyond the fixed indication marker or they assume a predetermined position in relation to each other, e.g. coincident with or close to each other, the physician can be sure that the helix is completely extended from the header sleeve. However, this does not necessarily imply that the helix also is completely embedded into tissue.

SUMMARY OF THE INVENTION

It is an object of the invention to provide an improved medical implantable lead, by which at least the above disadvantages can be avoided. More precisely, it is an object of the invention to provide a medical implantable lead by which the physician performing the attachment of the lead to an organ inside a body is able to get an indication of whether the attachment is properly performed or not. The invention also relates to a method for ensuring proper and safe attachment of a medical implantable lead to an organ, having essentially the same object as above.

Accordingly, the basis of the invention is the understanding that the above object may be achieved by arranging a movable member in a distal portion of the lead that is displaceable in an axial direction of the lead. The movable member is actuated by a resilient member in order to be, in an initial state, maximally protruded in a distal direction in relation to the lead. The movable member has a radiopaque material that forms a first indication marker. The lead also has a second indication marker of a radiopaque material in relation to which the movable member is displaceable. The first and the second indication markers are arranged such that, when observing the lead in an implanted state by means of fluoroscopy, it will be recognizable from the relative positions of the first and second indication markers, whether the distal end of the lead is in close contact with the surface of the tissue or not.

Within this general idea the invention can be varied in many different ways. According to embodiments of the invention, the lead has at its distal end, a movable member, which is displaceable in an axial direction of the lead and is actuated by a resilient member to be, in an initial state, maximally protruded in a distal direction in relation to the lead. The movable member is formed of or embodies a radiopaque material that forms a first indication marker, which is visible in an implanted state of the lead by means of fluoroscopy. Also, a second indication marker is arranged at the header with which the first indication marker is comparable, such that the relative positions of the first and second indication markers are indicative of whether the distal end of the header is in abutment with the tissue or not. The second indication marker can be fixedly positioned on the header or be positioned on an additional movable member, such as a movable shaft which carries a helix that can be screwed out from the outer portion of the lead, i.e. the header, by rotating and hence displacing of the shaft, as in hereinafter described and illustrated embodiments of the invention. Furthermore, the material in the rest of the header should be adapted such that the indication markers are visible, i.e. such that no other radiopaque material in the header prevents the visibility of the indication markers, neither in their initial positions nor in their positions when the lead is implanted and correctly attached to the tissue.

The relative positions of the first and second indication markers can be arranged in different ways. For example, both of the indication markers are visible in the initial state but they coincide in the correct attached state of the lead, they coincide in the initial state but both are visible, and e.g. separated by a small spacing, in the correct attached state, or both of them are visible in the initial state as well as in the correct attached state but have different relative positions. To facilitate distinguishing the first and second indication markers they may be formed with different sizes and/or different shapes.

In the hereinafter illustrated and described embodiments of the invention, the movable member constituting or comprising the first indication marker is formed as a sleeve having approximately the same diameter as the header, or as a pin being concentric with the header. However, other types of movable members could also be conceivable. The position of the movable member is to be compared with a second indication marker, such that it can be detected whether the distal end of the header abuts against the surface of the tissue or not. Within this general idea, the indication markers can be arranged in many different ways.

Also, the penetrating fixation element may be formed in different ways. Normally, as is illustrated in the embodiments hereinafter, it is in the form of a helix, which is screwed into the tissue. However it could be conceivable to use e.g. a straight needle having barbs or the like, though that kind of fixation element may have the disadvantage of being more difficult to detach from the tissue. Moreover, a helix can either be fixed in relation to the header, in which case the entire lead is rotated when screwing the helix into the tissue, it can be rotatable but non-extendable in relation to the header, or it can be rotatable and extendable in relation to the header. In the latter case, it is advantageous if the lead, in addition to a first and second indication marker for indication of proper abutment of the distal end of the header against the tissue, also comprises one or more indication markers for indication of whether the helix is screwed out to the maximum extent in relation to the header or not. Such an indication marker may comprise a helix made of a radiopaque material which can be compared with a radiopaque tip of the header to make it possible to see how many coils of the helix that is extended beyond the tip of the header.

BRIEF DESCRIPTION OF THE DRAWINGS

FIGS. 5, 6 and 7 show respective longitudinal sections through the distal end of a medical lead according to a second embodiment of the invention, in different stages of attachment.

FIGS. 8, 9, 10 and 11 show respective longitudinal sections through the distal end of a medical lead according to a third embodiment of the invention, in different stages of attachment.

FIGS. 20, 21, 22 and 23 show respective longitudinal sections through the distal end of a medical lead according to a sixth embodiment of the invention, in different stages of attachment.

DESCRIPTION OF THE PREFERRED EMBODIMENTS

Figure 1:
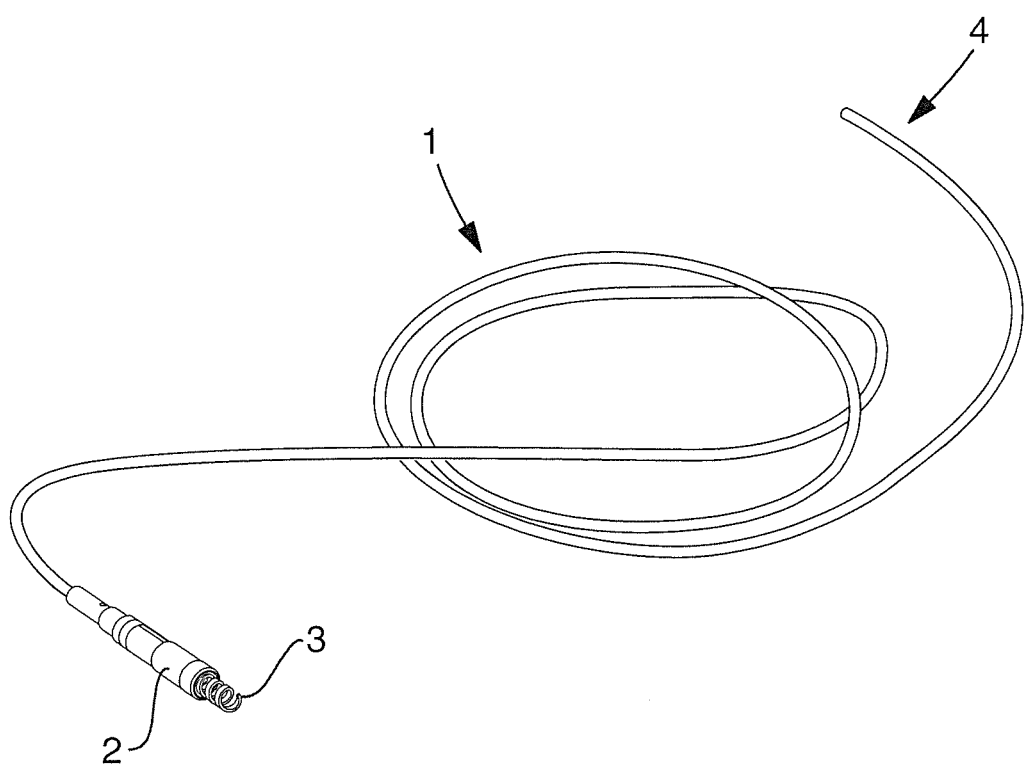
FIG. 1 is a perspective view of a medical implantable lead.

Reference is first made to FIG. 1 in which is illustrated a medical implantable lead 1 in a perspective view. In a distal portion the lead is provided with a header 2 containing a helix 3, which is to be screwed into an organ inside a body, e.g. a heart, for attaching the distal end to the organ. A proximal end 4 of the lead is, in a way known in the art, adapted to be connected to a not shown monitoring and/or controlling device, e.g. a pacemaker or a cardiac defibrillator.

In the longitudinal sections through the distal portion of the lead in FIGS. 2-23, are disclosed six different embodiments of a medical implantable lead according to the invention, in various states of attachment to tissue 5 of an organ. All of the embodiments comprise a sleeve formed header 2, a shaft 6 located inside the header and a helix 3 mounted to the shaft. Throughout the different drawings, elements of radiopaque materials are illustrated in black, whereas elements of materials not being radiopaque are cross-hatched or unfilled.

Figures 2, 3, 4:
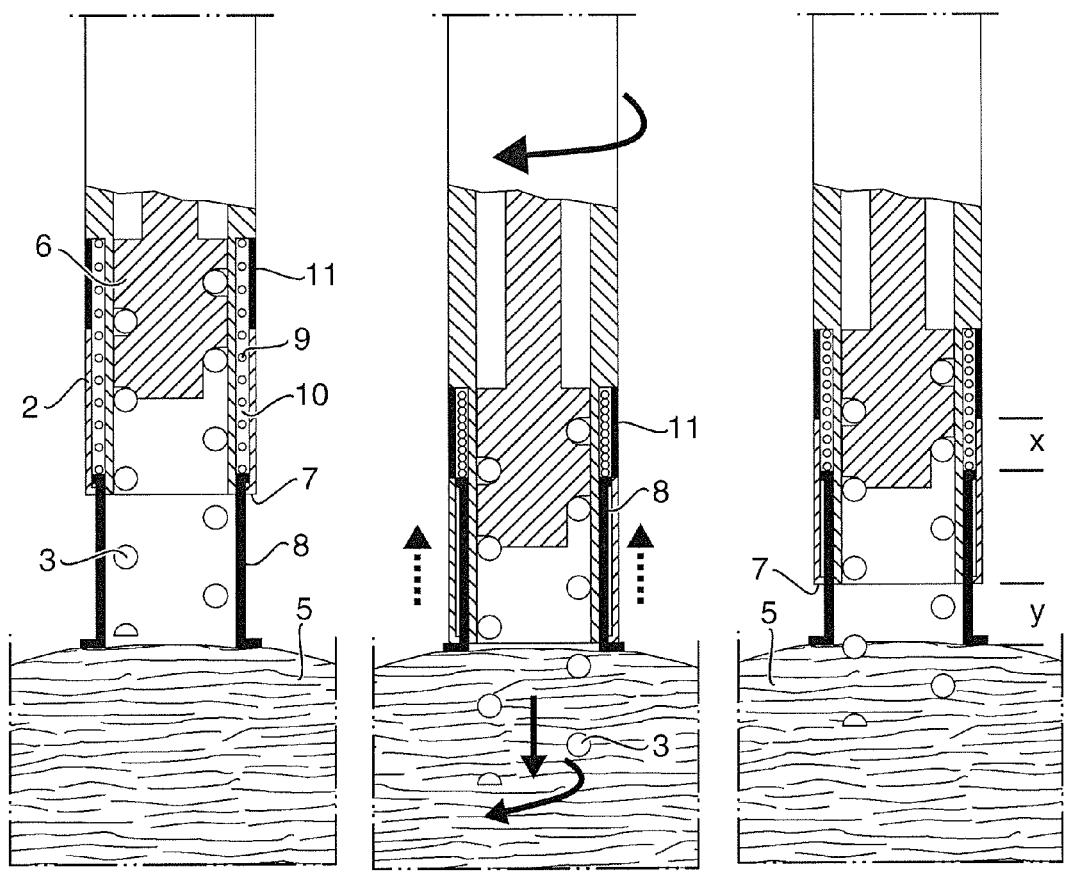
FIGS. 2, 3, and 4 show respective longitudinal sections through the distal end of a medical lead according to a first embodiment of the invention, in different stages of attachment.

A first embodiment of the invention is illustrated in FIGS. 2-4. In this embodiment the helix 3 is non-extendible from the header 2, which means that the helix is permanently protruded out from a distal end 7 of the lead and, in order to screw the helix into the tissue for attachment to the tissue, the entire lead is rotated or, alternatively, the shaft 6 is rotatable but non-extendibly arranged inside the header. In order to inter alia protect the helix and prevent it from accidentally penetrate into tissue in improper positions during insertion of the lead into the body, e.g. through veins or the like, the lead is provided with a movable sleeve 8, which is actuated by a spring 9 to protrude from the distal end 7 of the lead and to surround the distal portion of the helix in an initial state, as is illustrated in FIG. 2. The sleeve 8 as well as the spring 9 is accommodated inside a circular slot 10 arranged in the header 2, such that the sleeve is displaceable into the slot when abutting the distal end of the sleeve towards the tissue 5. This situation is illustrated in FIG. 3, in which the helix 3 is completely screwed into the tissue such that the distal end 7 is in abutment with the tissue and the sleeve is completely pushed into the slot against the action of the spring 9.

The sleeve as well as a ring 11, being positioned on the header at a small distance from the distal end of the lead, is of a radiopaque material such that they form first and second indication markers, respectively, which are visible when viewing the lead by means of fluoroscopy during implanting. The physician performing the implantation can then in an initial stage, as is illustrated in FIG. 2, see the sleeve and the ring at a comparatively long distance from each other before the lead is attached to the tissue. When the lead is correctly attached, as is illustrated in FIG. 3, the physician can see by means of fluoroscopy that there is no distance between the sleeve 8 and the ring 11, which is an indication that the attachment is correctly performed. When, on the other hand, the attachment of the lead to the tissue is not correctly performed, as is illustrated in FIG. 4, there will remain a gap x between the upper edge of the sleeve 8 and the lower edge of the ring 11 which will be visible on the X-ray image. The gap is an indicator that the helix 3 is not completely screwed into the tissue 5 such that the distal end 7 of the lead is not in abutment with the tissue. Instead, there remains a distance y between the distal end of the lead and the tissue. This has the effect that the engagement of the helix with the tissue will be poor and that the helix runs the risk of being disengaged. Also, a large portion of the helix will be in direct contact with body fluids, such as blood, which will increase the energy consumption and lead to a more rapid draining of a battery inside a monitoring and/or controlling device.

A second embodiment of the invention is disclosed in FIGS. 5-7. Also in this embodiment the helix 3 is permanently extended from the header 2 and protected by a sleeve 8, which is displaceable into a slot 10 in the header against the action of a spring 9. In analogy with the previous embodiment, the sleeve is of a radiopaque material for forming of a first movable indication marker. However, the second indication marker is in this embodiment in form of a portion 12 of radiopaque material in the shaft 6, such that the upper edge of the sleeve and the lower edge of the radiopaque portion 12, will be flush with each other when the lead is correctly attached, as is illustrated in FIG. 6, whereas a gap x will be present between the sleeve and the radiopaque portion on the shaft when the lead is incorrectly attached such that there is a distance y between the distal end 7 of the lead and the tissue 5, as is illustrated in FIG. 7. The radiopaque portion 12 will be visible through the header 2 since the latter is manufactured from a material being transparent for x-ray radiation.

FIGS. 8-11 illustrate a third embodiment of the invention. In this embodiment the helix 3 is extendible out from the header 2 by rotation of the shaft 6. Besides that, this embodiment presents many similarities with the first embodiment, such as a sleeve 8 of a radiopaque material, which forms a first indication marker and is movable inside a slot 10 in the header against the action of a spring 9. A second indication marker in form of a fixed ring 11 of a radiopaque material is arranged on a distance from the distal end 7 of the lead. In this embodiment also the helix 3 comprises a radiopaque material. In the initial state, as disclosed in FIG. 8, the sleeve as well as the helix protrudes a distance beyond the distal end of the lead. When rotating the shaft, it will be displaced toward the distal end of the lead and the helix will be extended out from the lead and screwed into the tissue 5, as can be seen in the illustration of a correctly attached lead in FIG. 9 in which the upper edge of the sleeve 8 and the lower edge of the ring 11 are flush to each other. Since the helix 3 comprises a radiopaque material, the physician performing the implantation can see when the helix is screwed out to the maximum extent by counting the number of coils of the helix that are visible beneath the lower edge of the sleeve 8. In the mounted state illustrated in FIG. 10, the upper edge of the sleeve 8 and the lower edge of the ring 11 are flush to each other. Despite this, the lead is not properly attached as can be seen by the few numbers of the helix coils which are visible beneath the lower edge of the sleeve. Accordingly, there is a risk that the lead will be detached from the tissue. In FIG. 11 is illustrated a state where the helix 3 is not completely screwed out from the header in combination with the distal end of the lead not being in contact with the tissue. The latter is detectable by the upper edge of the sleeve 8 and the lower edge of the ring 11, not being flush with each other but is forming a gap x.

Figure 12:
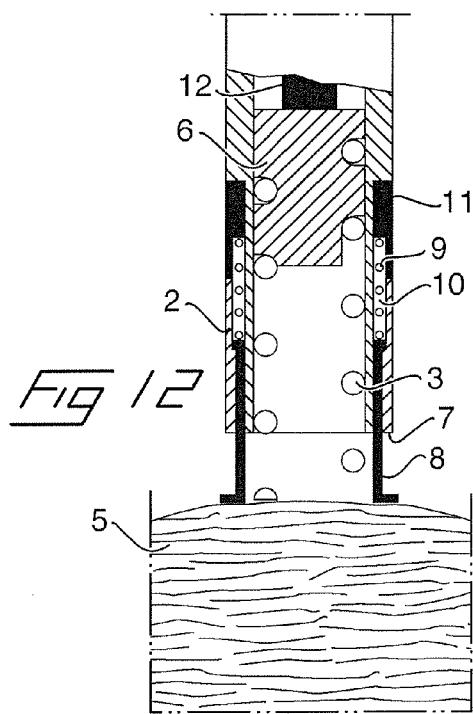
FIGS. 12, 13, 14 and 15 show respective longitudinal sections through the distal end of a medical lead according to a fourth embodiment of the invention, in different stages of attachment.
Figure 13:
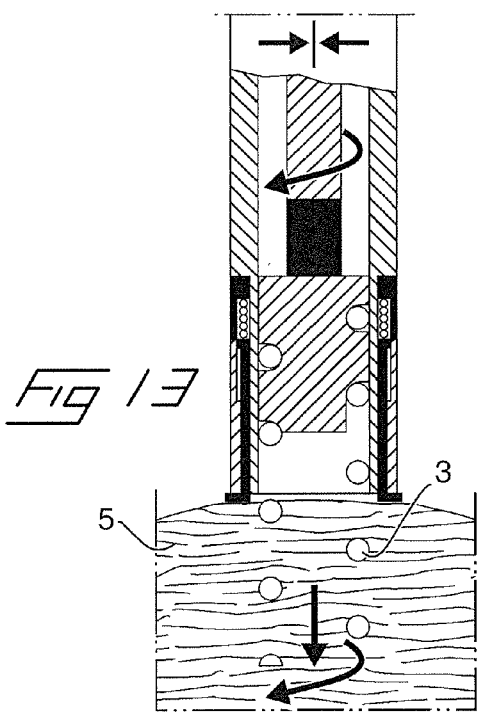
Figure 14:
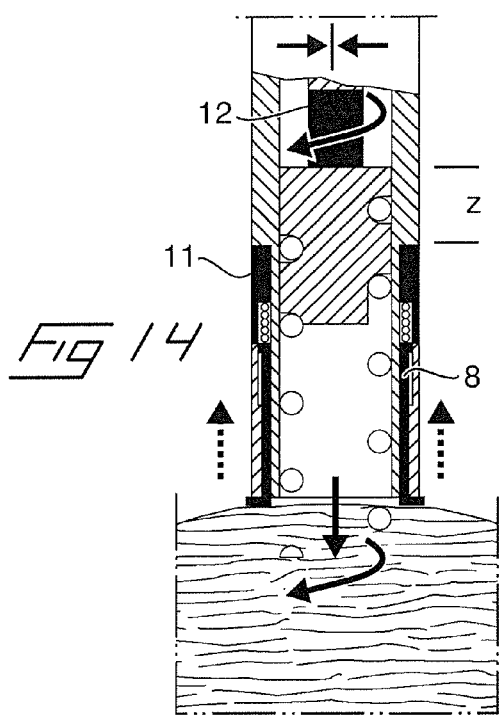
Figure 15:
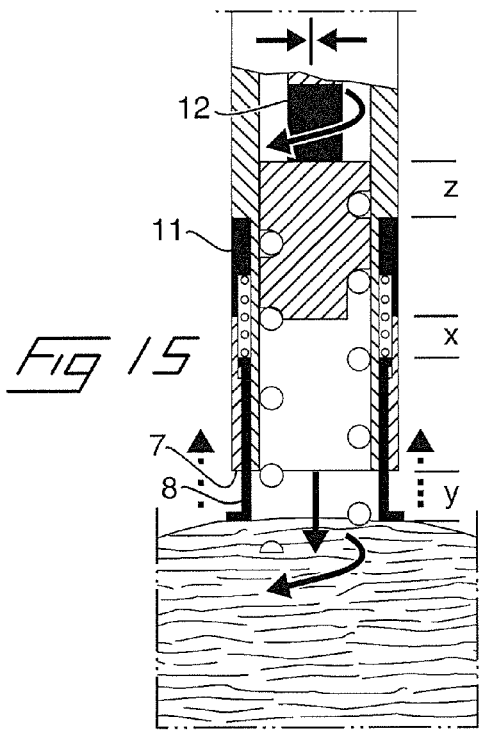

In analogy with the third embodiment, a fourth embodiment according to FIGS. 12-15 is provided with a helix 3, which is extendible out from the header 2 by rotation of the shaft 6, and a sleeve 8 which is movable against the action of a spring 9 inside a slot 10 in the header 2. The sleeve is of a radiopaque material and forms a first indication marker and the header is also provided with a ring 11 of a radiopaque material which forms a fixed second indication marker. However, in this embodiment the helix is formed of material that is transparent by fluoroscopy. Instead, the shaft is provided with a radiopaque portion 12. In FIG. 12 the lead is illustrated in an initial state having the sleeve protruded to the maximum extent in a distal direction and the helix being to the maximum extent screwed into the header. In FIG. 13 the lead is illustrated in a correct mounted state with the helix 3 screwed into the tissue 5 of the organ. In the correct mounted state an upper edge of the sleeve 8 is flush with a lower edge of the ring 11 and an upper edge of the ring is flush with a lower edge of the radiopaque portion 12 of the shaft. In FIG. 14 is illustrated a situation where the helix 3 is insufficiently screwed into the tissue 5, but where the distal end 7 of the lead is in abutment with the tissue. Accordingly, no gap is present between the sleeve and the ring but there is a gap z between the ring and the radiopaque portion of the shaft which indicates that the lead is improperly attached to the tissue. In FIG. 15, neither is the helix 3 completely screwed into the tissue 5, nor is the distal end 7 of the lead in contact with the tissue. This is detectable by means of fluoroscopy by a gap x between the sleeve and the ring as well as a gap z between the ring and the radiopaque portion of the shaft.

Figure 16:
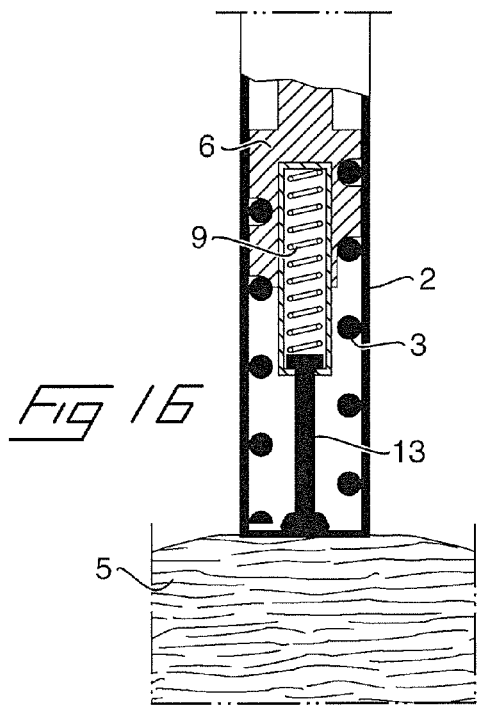
FIGS. 16, 17, 18 and 19 show respective longitudinal sections through the distal end of a medical lead according to a fifth embodiment of the invention, in different stages of attachment.
Figure 17:
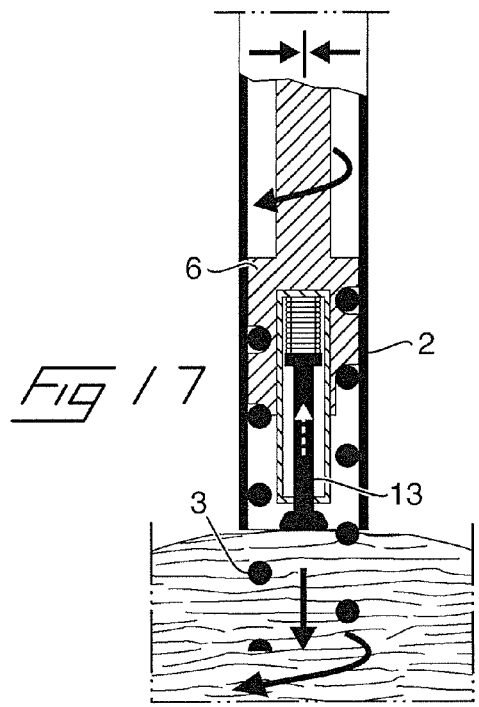
Figure 18:
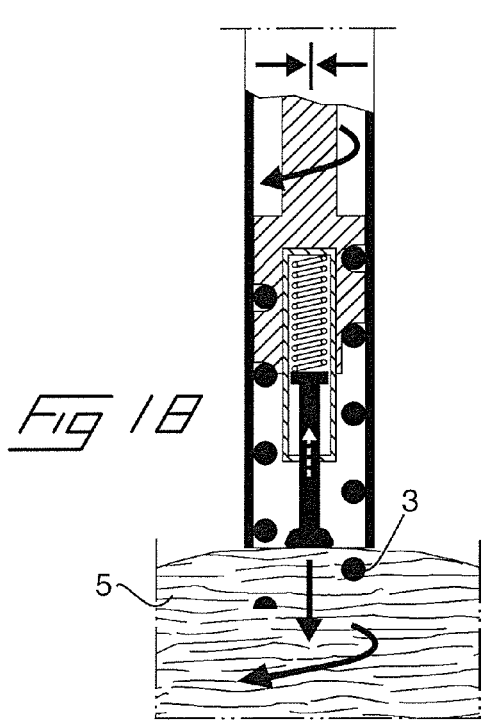
Figure 19:
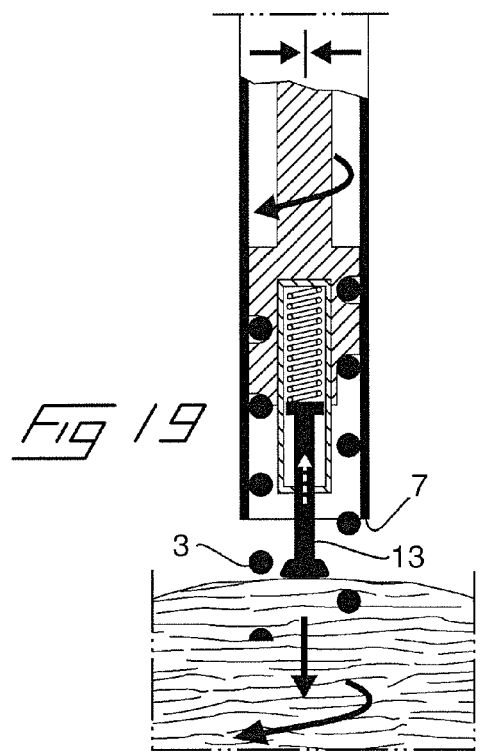

A fifth embodiment is illustrated in FIGS. 16-19 in which the helix 3 is extendible out from the header 2. Instead of a movable sleeve of a radiopaque material, this embodiment is provided with a movable pin 13, which is arranged in the centre of the shaft 6 and is actuated by a spring 9 to be maximally protruded in the distal direction of the lead. Moreover, the header as well as the helix is of radiopaque materials. An initial state is illustrated in FIG. 16 in which the helix is completely accommodated within the header and the pin is maximally extended such that its distal end is flush with the distal end of the header. When rotating the shaft 6 it will be displaced, together with the helix 3, in the distal direction such that the helix will be extended from the header, as is illustrated in FIG. 17 where the lead is correctly attached to the tissue. This is evident from fluoroscopy by counting the number of coils of the helix that is visible beneath the distal end of the header and by the fact that no part of the pin 13 is visible beneath the header 2. In FIG. 18 is illustrated a state where the distal end 7 of the lead is correctly in contact with the tissue 5, which is evident by the fact that no part of the pin 13 is visible beneath the header. However, the helix 3 is not completely screwed into the tissue which is evident by the few numbers of the coils of the helix which are visible beneath the header. In FIG. 19 the helix 3 is completely extended from the header 2 but the distal end 7 of the lead is not in contact with the tissue, which is evident by the distal portion of the pin 13 being visible beneath the header.

Similar to the fifth embodiment, a sixth embodiment according to FIGS. 20-23 comprises an extendable shaft 6 and helix 3 and a pin 13 is movably arranged in the centre of the shaft. However, in this embodiment the helix is not radiopaque, only a most distal ring portion 11 of the header is radiopaque and the shaft comprises a radiopaque portion 12. In an initial state as illustrated in FIG. 20, the shaft 6 and the helix 3 are completely withdrawn into the helix and the distal end of the pin 13 is flush with the distal end 7 of the header. A correct mounted state of the lead is disclosed in FIG. 21, where the distal end 7 of the lead is in contact with the tissue 5, as is evident by the distal portion of the pin 13 not being visible beneath the lower edge of the ring 11, and the helix 3 being maximally protruded from the header 2, as is evident by the lower edge of the radiopaque portion 12 of the shaft 6 being flush with the proximal end of the pin 13. In FIG. 22 is illustrated a state where the distal end 7 of the lead being properly in contact with the tissue 5, which is evident by the distal portion of the pin 13 not being visible beneath the distal end of the header. However, the helix is not completely extended from the header, which is evident by the gap z between the proximal end of the pin and the lower edge of the radiopaque portion 12 of the shaft. In FIG. 23 is disclosed another improper attachment of the lead. Here, the helix 3 is completely extended from the header, but the distal end 7 of the lead is not in contact with the tissue, as is seen by a distal portion of the pin 13 being visible beneath the distal end of the header.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for ensuring proper and safe attachment of a medical implantable lead to an organ inside a human or animal body for monitoring and/or controlling of the function of the organ by means of electrical signals, the medical implantable lead comprising an indication arrangement of a radiopaque material for visibility by means of fluoroscopy in an implanted state, the method comprising the steps of:

providing a displaceable first indication marker of a radiopaque material being movably arranged in relation to a distal portion of the lead which in an initial position protrudes an initial distance in a longitudinal direction from the distal end of the lead and is displaceable in a longitudinal axial direction of the lead against the action of a resilient member which acts to displace the displaceable first indication marker towards the initial distance;

providing a second indication marker, also of a radiopaque material, in relation to which the first indication marker is displaceable;

implanting the medical implantable lead inside the human or animal body by attaching a fixation element to the organ, wherein the displaceable first indication marker translates in a proximal direction in response to the fixation element penetrating the organ;

monitoring the attachment procedure by means of fluoroscopy; and comparing the relative positions of the first and second indication markers, which are indicative of whether the distal end of the medical implantable lead is in proper contact with the tissue or not.

2. A medical implantable lead comprising:

a lead body adapted for implantation in a human or animal body, said lead body having a distal portion terminating in a distal end, and an opposite proximal end;

a fixation element at said distal end of said lead body, said fixation element being adapted to penetrate in vivo through a surface of an organ to fix the lead body with the distal end in contact with the surface of the organ;

an electrode member adapted to receive electrical signals from, and/or transmit electrical signals to, the organ; and an indication arrangement at said distal portion of said lead body, said indication arrangement comprising a movable member that is displaceable in a longitudinal axial direction of said lead body by a resilient member to be, in an initial state, maximally extended in a distal direction relative to said lead, wherein the movable member translates in a proximal direction in response to the fixation element penetrating the organ, said movable member comprising radiopaque material that is fluoroscopically visible and that forms a first indication marker, and said indication arrangement further comprising a second indication marker formed of radiopaque material that is fluoroscopically visible, said movable member being displaceable relative to said second indication marker, and said first and second indication markers being located with respect to each other to produce an indication, by the relative positions of the first and second indication markers when fluoroscopically viewed, whether the distal end of the lead body is in close contact with the surface of the organ or not.

3. A medical implantable lead as claimed in claim 2 wherein said first and second indication markers have respectively different physical appearances, selected from the group consisting of different shapes and different sizes, to make said first and second markers fluoroscopically distinguishable.

4. A medical implantable lead as claimed in claim 2 wherein said first indication marker forms a movable sleeve.

5. A medical implantable lead as claimed in claim 2 wherein said fixation element is a rotatable helix.

6. A medical implantable lead as claimed in claim 2 wherein said fixation element is electrically conductive and forms an electrode.

7. A medical implantable lead as claimed in claim 2 wherein said second indication marker is mounted in a fixed position at said distal portion of said lead body.

8. A medical implantable lead as claimed in claim 2 wherein said movable member is a first movable member, and wherein said indication arrangement comprises a second movable member, at which said second indication marker is mounted.

9. A medical implantable lead as claimed in claim 2, wherein said first indication marker is arranged on a movable sleeve.

* * * * *